United States Patent
Talamini et al.

(10) Patent No.: US 12,310,739 B2
(45) Date of Patent: *May 27, 2025

(54) ASSEMBLY, METHOD AND COMPUTER PROGRAM PRODUCT FOR INFLUENCING A BIOLOGICAL PROCESS

(71) Applicants: Universiteit van Amsterdam, Amsterdam (NL); Deep Sleep Technologies B. V., Amsterdam (NL)

(72) Inventors: Lucia Maddalena Talamini, Amsterdam (NL); Ilia Korjoukov, Moscow (RU)

(73) Assignees: DeepSleep Technologies B.V., Amsterdam (NL); Universiteit van Amsterdam, Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/883,987

(22) Filed: Sep. 12, 2024

(65) Prior Publication Data
US 2025/0000429 A1    Jan. 2, 2025

Related U.S. Application Data

(63) Continuation of application No. 16/489,333, filed as application No. PCT/NL2018/050116 on Feb. 22, 2018.

(30) Foreign Application Priority Data

Feb. 27, 2017 (NL) .................................. 2018435

(51) Int. Cl.
*A61B 5/374*    (2021.01)
*A61B 5/00*    (2006.01)
(Continued)

(52) U.S. Cl.
CPC .............. *A61B 5/374* (2021.01); *A61B 5/316* (2021.01); *A61B 5/378* (2021.01); *A61B 5/38* (2021.01); *A61B 5/7275* (2013.01)

(58) Field of Classification Search
None
See application file for complete search history.

(56) References Cited

U.S. PATENT DOCUMENTS

| | | |
|---|---|---|
| 2008/0194981 A1 | 8/2008 | Sarkela et al. |
| 2009/0018458 A1 | 1/2009 | Cao |

(Continued)

FOREIGN PATENT DOCUMENTS

| | | |
|---|---|---|
| WO | 2016028635 A1 | 2/2016 |
| WO | 2016166202 A1 | 10/2016 |
| WO | 2018156021 A1 | 8/2018 |

OTHER PUBLICATIONS

Blinowska et al., "Non-linear and linear forecasting of the EEG time series", Biological Cybernetics, vol. 66, 1991, pp. 159-165.

(Continued)

*Primary Examiner* — Jacqueline Cheng
*Assistant Examiner* — Samuel C Kim
(74) *Attorney, Agent, or Firm* — Occhiuti & Rohlicek LLP (57) ABSTRACT

The invention provides an assembly comprising:
  a recording assembly for recording a time-based brain-related signal;
  a stimulus generator for providing a stimulus, and
  a computer assembly, functionally coupled to said recording assembly and to said stimulus generator, said computer assembly comprising:
  a memory for storing at least a data segment of said time-based brain-related signal during recording of said time-based brain-related signal, and
  (Continued)

a computer program which, when running on said computer assembly, functionally real-time performs:

retrieving a most-recent data segment of said stored data segment of said time-based brain-related signal;

fitting at least one curve to said retrieved most-recent data segment;

predicting a future continuation of said most-recent data segment using said at least one curve fitted to said most-recent data segment;

detecting a predefined pattern in said predicted future continuation for predicting occurrence of said predefined pattern, and defining a predicted event time of said predefined pattern, said predicted event time being in the future with respect to said most-recent data segment, and actuating said stimulus generator for providing a stimulus within a predefined event time window of said predicted event time.

24 Claims, 3 Drawing Sheets

(51) Int. Cl.
*A61B 5/316* (2021.01)
*A61B 5/378* (2021.01)
*A61B 5/38* (2021.01)

(56) References Cited

U.S. PATENT DOCUMENTS

| | | |
|---|---|---|
| 2010/0168604 A1 | 7/2010 | Echauz et al. |
| 2011/0098933 A1 | 4/2011 | Ochs |
| 2014/0273042 A1 | 9/2014 | Saint |
| 2015/0164361 A1 | 6/2015 | Lunner |
| 2015/0272465 A1 | 10/2015 | Ishii |
| 2016/0081617 A1 | 3/2016 | Iyer |
| 2016/0082222 A1 | 3/2016 | Garcia Molina et al. |
| 2016/0220141 A1 | 8/2016 | Thornton |
| 2016/0317807 A1 | 11/2016 | Ma et al. |
| 2017/0360356 A1 | 12/2017 | Ashdown et al. |

OTHER PUBLICATIONS

Cox, R. et al; "Sound Asleep: Processing and Retention of Slow Oscillation Phase-Targeted Stimuli"; PLOS ONE, Jul. 2014, vol. 9, Issue 7, e101567.

L. Leon Chen et al: Real-Time Brain Oscillation Detection and Phase-Locked Stimulation Using Autoregressive Spectral Estimation and Time-Series Forward Prediction Published in: IEEE Transactions on Biomedical Engineering ( vol. 60 , Issue: 3 , Mar. 2013) pp. 753-762, DOI: 10.1109/TBME.2011.2109715.

International Search Report and Written Opinion of the International Searching Authority for PCT/NL2018/050116 mailed Jul. 11, 2018.

ASSEMBLY, METHOD AND COMPUTER PROGRAM PRODUCT FOR INFLUENCING A BIOLOGICAL PROCESS

FIELD OF THE INVENTION

The invention relates to an assembly, a method, and a computer program product for influencing a biological process.

BACKGROUND OF THE INVENTION

US20150272465 according to its abstract describes: "A portable neurofeedback device is described. The neurofeedback device includes a wearable fixture. One or more brainwave sensors are attached to the wearable fixture. A processing unit is attached to the wearable fixture. The processing unit receives brainwave signals captured by the one or more brainwave sensors. The processing unit computes one or more user-feedback values that represent current brain activity. A display module is attached to the wearable fixture that displays a visual representation of the one or more user-feedback values."

US20160081617 according to its abstract describes: "A patient monitoring system includes an electroencephalography (EEG) monitor and an EEG sensor array. The EEG sensor array includes a plurality of electrodes configured to acquire EEG signals from a patient. The EEG monitor may be configured to calculate one or more depth of anesthesia indices for the patient based on received EEG signals from the EEG sensor array. Additionally, the EEG monitor may be configured to generate and display a topographic color map of the calculated depth of anesthesia indices."

US20160220141 according to its abstract describes: "Mental abilities are labeled with terms such as memory & problem solving and corresponding performance measures (recall score, # correct) can be obtained. The quantitative EEG (QEEG) measure of brain functioning reflects the electrophysiology of the gray & white matter of the brain underlying the scalp. A database of clinical and non-clinical participants underwent a cognitive activation QEEG to determine the relations between the QEEG measures and cognitive performance for memory (auditory and reading) and problem solving. The analysis revealed correlative (positive and negative) relationships between cognitive performance and the Quantitative EEG (QEEG) measures (coherence, phase, magnitude, etc.) during these cognitive activation conditions. An individual can undergo an evaluation and the subject's values on the relevant (and all) variables can be determined. The deficient QEEG variables can be effectively changed with an operant biofeedback conditioning methodology called EEG biofeedback. The method has been shown to improve memory functioning."

WO2016028635 according to its abstract describes: "Certain examples provide systems and methods to enhance slow wave sleep. An example method includes identifying a sleep stage for slow wave sleep in a subject being monitored. The example method also includes generating, following identification of slow wave sleep and using a processor including a phase locked loop, an output signal based on a phase of a reference input signal, the output signal phase locked according to the reference input signal. The example method includes delivering, during slow wave sleep for the subject, a stimulus to the subject based on the phase locked output signal. The delivering includes providing the stimulus in a series of signal pulses for a first period of time; and providing a refractory period without pulses in a second period of time. The method further includes measuring feedback from the stimulus."

In Roy Cox, Ilia Korjoukov, Marieke de Boer, Lucia M. Talamini, "Sound Asleep: Processing and Retention of Slow Oscillation Phase-Targeted Stimuli", PLOS ONE, July 2014, Vol. 9, Issue 7, e101567, according to its abstract is described "The sleeping brain retains some residual information processing capacity. Although direct evidence is scarce, a substantial literature suggests the phase of slow oscillations during deep sleep to be an important determinant for stimulus processing. Here, we introduce an algorithm for predicting slow oscillations in real-time. Using this approach to present stimuli directed at both oscillatory up and down states, we show neural stimulus processing depends importantly on the slow oscillation phase. During ensuing wakefulness, however, we did not observe differential brain or behavioral responses to these stimulus categories, suggesting no enduring memories were formed. We speculate that while simpler forms of learning may occur during sleep, neocortically based memories are not readily established during deep sleep.".

Leon Chen, L., et al.: "Real time Real-Time Brain Oscillation Detection and Phase-Locked Stimulation Using Auto regressive Spectral Estimation and Time-Series Forward Prediction", IEEE TRANSACTIONS ON BIOMEDICAL ENGINEERING, IEEE SERVICE CENTER, PISCATAWAY, NJ, USA, part 60, no. 3, 1 Mar. 2013 (2013 Mar. 1), pp 753-762 in its abstract describes: "Neural oscillations are important features in a working central nervous system, facilitating efficient communication across large networks of neurons. They are implicated in a diverse range of processes such as synchronization and synaptic plasticity, and can be seen in a variety of cognitive processes. For example, hippocampal theta oscillations are thought to be a crucial component of memory encoding and retrieval. To better study the role of these oscillations in various cognitive processes, and to be able to build clinical applications around them, accurate and precise estimations of the instantaneous frequency and phase are required. Here, we present methodology based on autoregressive modeling to accomplish this in real time. This allows the targeting of stimulation to a specific phase of a detected oscillation. We first assess performance of the algorithm on two signals where the exact phase and frequency are known. Then, using intracranial EEG recorded from two patients performing a Sternberg memory task, we characterize our algorithm's phase-locking performance on physiologic theta oscillations: optimizing algorithm parameters on the first patient using a genetic algorithm, we carried out cross-validation procedures on subsequent trials and electrodes within the same patient, as well as on data recorded from the second patient."

US2016082222 according to its abstract describes "A system is configured to provide sensory stimuli to a subject at a first intensity level, determine the effectiveness of the provided sensory stimuli, and incrementally increase the intensity level of the sensory stimuli based on the determined effectiveness. The effectiveness determination and the corresponding intensity increase are repeated one or more times during a given slow wave sleep episode. The system is configured to continue the effectiveness determinations and the corresponding intensity increases during the slow wave sleep episode until the intensity level reaches a maximum level, until an arousal level of the subject breaches an arousal level threshold, and/or until expiration of the period of slow wave sleep.

SUMMARY OF THE INVENTION

In the prior art, influencing a biological process, for instance sleep, was found difficult if not impossible. In particular, influencing a brain-related signal was found difficult if not impossible, in particular for faster changing signals.

Hence, it is an aspect of the invention to provide an alternative assembly or method that allows influencing a biological process using at least one sensory discernible stimulus. In particular, the invention seeks to influence a brain-related signal by using a sensory-discernible stimulus. The assembly and/or method further at least partly obviates one or more of above-described drawbacks. The invention thus relates to an assembly comprising:

a recording assembly for recording a time-based brain-related signal;
a stimulus generator for providing a stimulus, and
a computer assembly, functionally coupled to said recording assembly and to said stimulus generator, said computer assembly comprising:
a memory for storing at least a data segment of said time-based brain-related signal during recording of said time-based brain-related signal, and
a computer program which, when running on said computer assembly, functionally real-time performs:
retrieving a most-recent data segment of said stored data segment of said time-based brain-related signal;
fitting at least one curve to said retrieved most-recent data segment;
predicting a future continuation of said most-recent data segment using said at least one curve fitted to said most-recent data segment;
detecting a predefined pattern in said predicted future continuation for predicting occurrence of said predefined pattern, and defining a predicted event time of said predefined pattern, said predicted event time being in the future with respect to said most-recent data segment, and
actuating said stimulus generator for providing a stimulus within a predefined event time window of said predicted event time.

The invention further relates to a method for influencing a biological process, said method comprising
recording a time-based brain-related signal;
performing real-time fitting of at least one curve to a most-recent data segment of said brain-related signal;
predicting a future continuation of the recorded signal using said curve fitted to said data segment;
detecting a predefined pattern in said predicted future continuation and defining a predicted event time of said predefined pattern, and
providing a stimulus within an event window of said predicted event time if said predefined pattern is detected in said future continuation.

The invention further pertains to a computer program product, wherein said computer program product, when running on a computers system, performs:
retrieve a time-based brain-related signal;
performing real-time fitting of at least one curve to a most-recent data segment of said brain-related signal;
predicting a future continuation of the recorded signal using said curve fitted to said data segment;
detecting a predefined pattern in said predicted future continuation and defining a predicted event time of said predefined pattern, and
actuate generation of a stimulus within an event window of said predicted event time if said predefined pattern is detected in said future continuation.

In neuroscience, a setup as claimed may be referred to as a comprising a "closed loop". In control theory, a closed-loop transfer function is an algorithm that describes the net result of the effects of a feedback loop on an input signal to the circuits enclosed by the loop. Here, a feedback loop is provided in that a measurement of a brain-related signal is done, an event is predicted at an event time, and a stimulus is provided at said predicted event time and that influences that brain-related signal.

The predefined pattern can be any pattern in a brain-relates signal that is or can be linked to a functioning of a subject. Examples of such predefined patterns are for instance rising and/or declining flanks of a brain-related signal.

In an embodiment, the brain-related signal originates from a mammal. In particular, the brain-related signal originates from a human. A stimulus can be any stimulus that can be applied. In particular, a stimulus can be a stimulus that can be applied to a human being. Such a stimuli in an embodiment can be selected from an electromagnetic stimulus, or a sensory perceivable stimulus. Examples of stimuli that can be applied are any stimulus that is discernible by a mammal, in particular by a human being. Such a stimulus can for instance be audible, visible, sensible, palpable, smellable.

In Wikipedia, it is defined as follows: Humans have a multitude of senses. Sight (vision), hearing (audition), taste (gustation), smell (olfaction), and touch (somatosensation) are the five traditionally recognized senses. The ability to detect other stimuli beyond those governed by these most broadly recognized senses also exists, and these sensory modalities include temperature (thermoception), kinaesthetic sense (proprioception), pain (nociception), balance (equilibrioception), vibration (mechanoreception), and various internal stimuli (e.g. the different chemoreceptors for detecting salt and carbon dioxide concentrations in the blood). Some species are able to sense electrical and magnetic fields, and detect water pressure and currents. Wikipedia also identifies "non-traditional senses", which may also be a subject of the stimulus according to the invention, including: Balance and acceleration, Temperature, Proprioception, Pain, and "Other internal senses".

From the above, it will be evident to s skilled person what the nature is of these stimuli and how to apply them. In particular, the current invention relates to stimuli that influence the brain.

In an embodiment, a stimulus can be a so-called phase-targeted stimuli, i.e., a stimulus that is applied when a predefined phase occurs.

EEG patterns that develop much faster than slow oscillations or spindle power envelopes, can for instance be targeted by the current assembly and/or method. These slow oscillations are among the slowest developing EEG patterns, around 0.5-1 Hz. It may further be possible that alpha waves, i.e., 8-12 Hz waves, can be successfully targeted. Additionally, targeting waves at least up to about 16 Hz is possible. Using the direct, unfiltered EEG signal and predicting its course, and subsequently finding an event in the predicted signal, it was found to be possible to not only provide a targeted stimulus for slow frequency signals, but to also target relatively higher frequency signals. The current assembly and/or method allow for instance stimulation at an so-called up state of an EEG signal, but also allows targeting other features, like a down state. Using the unfiltered EEG signal allowed to used the most-recent data segment, allowing an accurate prediction.

The assembly can for instance be incorporated into commercially marketable applications. Examples of such applications are computer games, sleep improving wearables or appliances, phone apps, and the like.

The assembly and/or method can be used to manipulate memories during sleep. SO up-states have been shown to be conducive to the sleeping brain's processing of both externally presented stimuli and internally reactivated memories. Targeting of memory cues for pre-sleep learned material to slow oscillation up-states, improves later memory for the associated material, like foreign vocabulary. This represents a highly innovative application of the current assembly and/or method.

The assembly and or method can further be applied for enhancing sleep.

The current assembly and/or method induces slow oscillation trains after a single slow oscillation up state locked sound stimulus. The assembly or method can use for instance repetitive sound stimulation during sleep to enhance slow oscillations during stimulation Moreover, the current assembly and/or method are able to induce stimulation of deep sleep (i.e. slow wave sleep; SWS), e.g. in terms of longer SWS or more overall SO power during sleep. The current assembly and/or method can result in more effective slow oscillation boosting, even with single spread out stimuli. Indeed, each SO-up state targeted stimulus evokes a train of slow oscillations after stimulation. The assembly and/or method may be able to enhance deep sleep in general, and therewith all the cognitive and health benefits associated to deep sleep. Moreover, the current assembly and/or method may require fewer stimuli during sleep, have reduced risks of leading to arousals and thus, counteractive, adverse effects on sleep.

The current assembly and/or method may be applied on attention manipulation.

Generalized alpha oscillations have been show to be related to a relaxed mind state. In addition, strong localized alpha activity in a particular cortical area is related to active inhibition of that area when attention is directed to aspects of stimuli processed in other brain areas ('alpha inhibition'). Stimulus perception in relation to alpha phase have shown that perception is facilitated in the depolarized (less inhibited) part of the alpha cycle.

The current assembly and/or method can accurately target stimuli to specific alpha phases. It may thus be possible to enhance general alpha to promote a relaxation, e.g. in the context of anti stress therapy. Also it might be possible to stimulate local alpha in particular brain areas to suppress processing of distractors in a task, therewith aiding focused attention on relevant information.

In an embodiment, Curve fitting is the process of constructing a curve, or mathematical function, that has the best fit to a series of data points. This may be subject to constraints. In an embodiment, non-linear regression may be applied. nonlinear regression may be defined as a form of regression analysis in which observational data are modeled by a function which is a nonlinear combination of the model parameters and depends on one or more independent variables. The data are fitted by a method of successive approximations. The best-fit curve in am embodiment is one that minimizes the sum of squared residuals. This is also referred to as the (ordinary) least squares (OLS) approach. However, in cases where the dependent variable does not have constant variance, a sum of weighted squared residuals may be minimized. This is also referred to as weighted least squares. In an embodiment, weights are equal to the reciprocal of the variance of the observation. These weights may be recomputed on each iteration when applying an iteratively weighted least squares algorithm.

In an embodiment, said prediction extending at least 0.5 seconds beyond the end time of said data segment, in particular at least 0.5 seconds past a current time of the assembly.

In an embodiment, said stimulus generator is arranged for applying a sensory discernible stimulus, in particular a sound or light stimulus that can be perceived by a human.

In an embodiment, said computer program is adapted for retrieving a most-recent data segment that has an end time that is less than 0.5 seconds from an assembly current time, in particular less than 0.1 second, more in particular less than 1 millisecond.

In an embodiment, said event time is in the future with respect to a current time of said assembly, allowing said assembly to apply said stimulus within said event time window.

In an embodiment, said curve fitting comprises applying a non-linear regression algorithm.

In an embodiment, said computer program retrieves said most-recent data segment within a processing time from its recording, in particular said processing time is less than 0.5 seconds, more in particular less than 0.1 seconds, more in particular less than 1 millisecond.

In an embodiment, said at least one curve comprises a series of periodic functions.

In an embodiment, said at least one curve comprises a series of trigonometric functions, in particular sinus functions.

In an embodiment, said computer program further evaluates a reliability of said fit, and if said reliability is within a predefined criterion, calculates said future continuation.

In an embodiment, said computer program retrieves a most-recent data segment with a data window of which has a width of less then 1 second, in particular less then 0.5 seconds.

In an embodiment, said computer program fits at least one periodic function to said most-recent data segment, said at least one periodic function having a period shorter then 2 seconds, in particular shorter then 0.2 seconds, more in particular shorter than 0.1 seconds.

In an embodiment, said brain-related signal comprises an electromagnetic signal, in particular an electro encephalogram (EEG).

In an embodiment, said EEG has a time resolution of at least 100 samples per second, more in particular at least 500 samples per second.

In an embodiment, said event is a predefined oscillatory phase in said brain-related signal, more in particular selected from a rising and a falling slope in said brain-related signal.

In an embodiment of said method, said stimulus is sensory detectable or discernible by a human subject.

In an embodiment of said method, the brain-related signal comprises an electroencephalogram (EEG), and the event time is less that 1 second beyond an end time of said data segment.

In an embodiment of said method, the most-recent data segment has a time window of less then 1 second, in particular less then 0.5 second, in particular said most-recent data segment comprising at least 100 data points, more in particular at least 500 data points.

In an embodiment of said method, the stimulus is provided functionally real-time in response to said detected predefined pattern in said future continuation, said real time being functionally real-time with respect to a typical time scale of said biological process.

In an embodiment of said method, the predefined pattern has a frequency of more than 1 Hz, in particular more than 7 Hz (alpha waves), more in particular more than 15 Hz.

The different embodiments separately or in combination allow functionally real-time evaluation of brain-related signals and application of a stimulus that influences a biological process.

The invention further relates to a closed-loop stimulation assembly adapted for presentation of stimuli in alignment with at least one predefined pattern in an ongoing biophysical, time-based brain-related signal, comprising a closed-loop procedure for targeting stimuli to selected phases of EEG oscillations, for differential processing of stimuli presented in slow oscillation up- and down-states oscillatory phase targeting. In such an assembly, in an embodiment, it is further adapted for applying an oscillatory phase prediction algorithm, based on non-linear fitting on data segments of an unfiltered EEG signal, and wherein the criteria for stimulus release comprise at least one selected from a fitted sine that is in a predefined frequency range of interest, reaching a fitting error threshold, reaching a relative power threshold in the frequency range of interest, or a combination thereof.

In such an assembly, in an embodiment, the assembly is adapted for a slow oscillation and/or alpha frequency range of said EEG, in on-line, real time EEG recordings.

The terms "upstream" and "downstream", when used, relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

The term "substantially" herein, such as in or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" will be understood by, and be clear to, a person skilled in the art. The term "substantially" as well as "functionally" may also include embodiments with "entirely", "completely", "all", etc. Hence, in embodiments the adjective functionally may also be removed. When used, for instance in "functionally parallel", a skilled person will understand that the adjective "functionally" includes the term substantially as explained above. Functionally in particular is to be understood to include a configuration of features that allows these features to function as if the adjective "functionally" was not present. The term "functionally" is intended to cover variations in the feature to which it refers, and which variations are such that in the functional use of the feature, possibly in combination with other features it relates to in the invention, that combination of features is able to operate or function. For instance, if an antenna is functionally coupled or functionally connected to a communication device, received electromagnetic signals that are receives by the antenna can be used by the communication device. The word "functionally" as for instance used in "functionally parallel" is used to cover exactly parallel, but also the embodiments that are covered by the word "substantially" explained above. For instance, "functionally parallel" relates to embodiments that in operation function as if the parts are for instance parallel. This covers embodiments for which it is clear to a skilled person that it operates within its intended field of use as if it were parallel.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus or device comprising one or more of the characterising features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the assembly and method will now be described, by way of example only, with reference to the accompanying schematic drawings in which corresponding reference symbols indicate corresponding parts, and in which.

The drawings are not necessarily on scale

DESCRIPTION OF PREFERRED EMBODIMENTS

Figure 1:
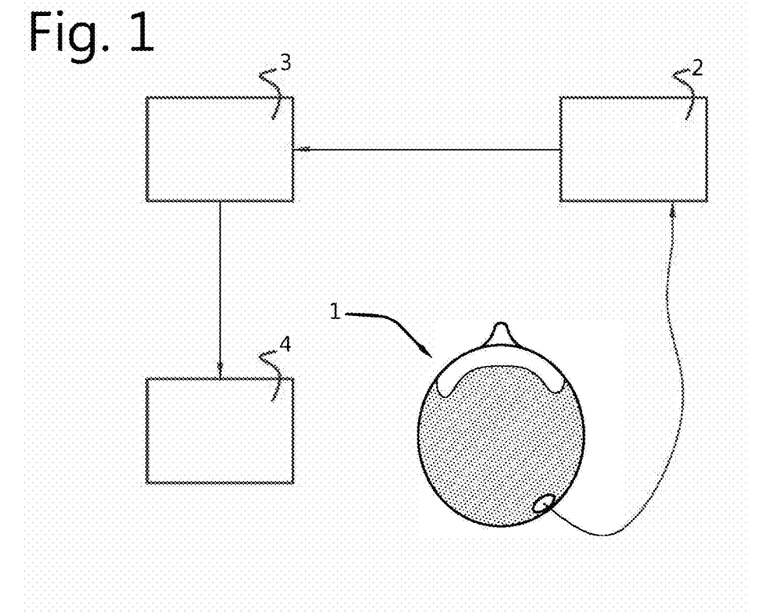
FIG. 1 schematically depicts an embodiment of an assembly.
Figure 2:
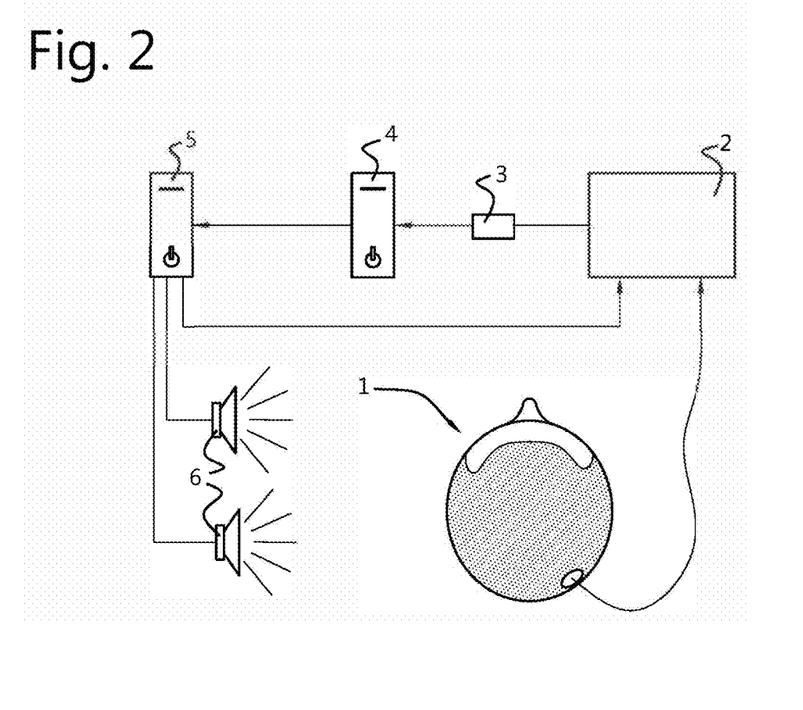
FIG. 2 schematically depicts a further embodiment of an assembly.

In FIGS. 1 and 2, several possible layouts of assemblies are indicated.

In FIG. 1, a (human) subject 1 is coupled to a recording assembly 2, here comprising an electrode coupled to an electroencephalogram (EEG) recording device. The recording device is coupled to a computer assembly 3 comprising a memory for storing a data segment of recorded signal from the recording assembly 2. The computer assembly 3 is functionally coupled to a stimulus generator 4 for generating a sensory discernible stimulus upon activation by said computer assembly 3.

In FIG. 2, the stimulus generator comprises a set of speakers for providing a sound signal as stimulus. In the embodiment of FIG. 2, the brain-related signal from subject 1 is first amplified using an amplifier and then transmitted using a glass fiber coupling to a data processor which records an EEG signal. The data processor is coupled to a computer system, here via a wired coupling over data cable. On the computer system, again the computer program runs which real-time retrieve a most recent segment of said recorded time-based data segment, said data segment having an end time, fits at least one curve to said retrieved data segment, predicts a future continuation of said recorded signal using said at least one curve fitted to said data segment, detects a predefined pattern in said predicted future continuation, and defining a predicted event time of said predefined pattern, and subsequently actuating said stimulus generator for providing a stimulus at said predicted event time.

An example of the equipment and software which can be used in the current assembly is summed below.
  72-channel Refa Amplifier (TMSi)
    64-channel EEG cap WaveGuard original (ANT-neuro) customized version of PolyBench software (TMSi; adapted by UvA, with working data stream)
    EventIDE software (Okazolab), a software package for experiment control and stimulus presentation, which hosts an algorithm for real-time EEG analysis.
Generic Equipment/Software
Computer 1 (Algorithm) with:
  Intel Core i5-4690 CPU @ 3.50 GHz processor
  16.0 GB RAM intern memory
  2× network card
  Sound Blaster Z-series sound card
  LPT port (parallel/printer port)
  GeForce GTX 750 video card
Computer 2 (EEG Recording) with:
  Intel Core i5-2500 CPU @ 3.30 GHz processor
  8.00 GB RAM intern memory
  465 GB SSD extra hard disk
  2× network card
Further Equipment:
  Cross-over network cable cat.6, max. 1 m length
  2× Creative speakers Gigaworks T20 series II In FIG. 3, part of a result of the assembly and method is shown. An EEG recording is plotted against time in milliseconds, thus actually showing a time of 10 seconds. Between the two vertical lines at about t=−2000 and t=0, a data segment is indicated. This most recent time window is used for curve fitting. In this plot, t=0 is the current time, and the past is indicated with negative times. Thus, the time scale shows 8 seconds (8000 milliseconds) in the past, and 2 seconds (2000 milliseconds) in the future.

Figure 3:
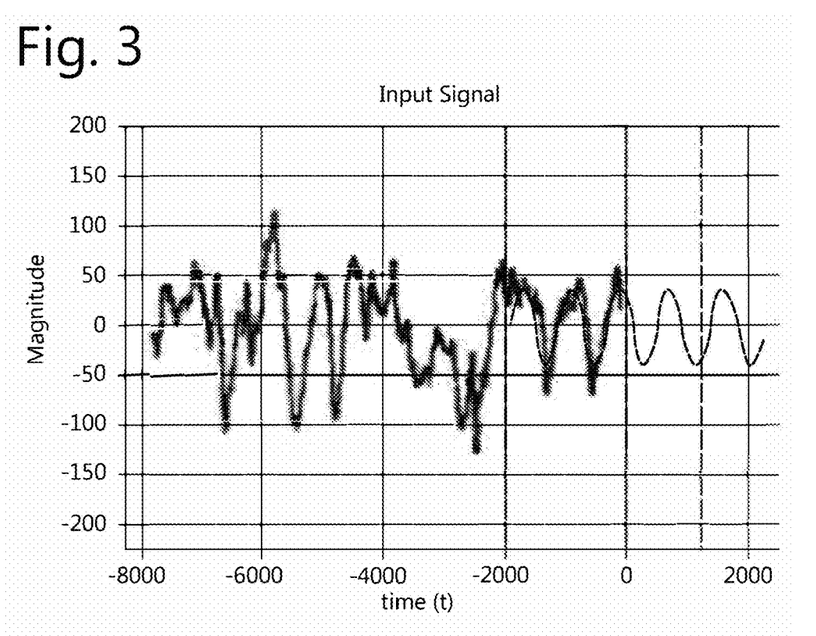
FIG. 3 shows an EEG recording with prediction.

On the data segment in the most recent time window, a curve is fitted to the recorded EEG. The fitted curve is indicated as a dotted line.

Beyond the vertical line at t=0 and further to the right, the future, a prediction is plotted that is based upon the fitted curve that was fitted on the data segment. Here the prediction is in a prediction time window between the vertical lines at t=0 and about t=1200, which thus is 1.2 second in the future. The prediction time window is thus 1200 milliseconds.

It should be clear that t=0 actually is not the current time or "now", but just a little while later. This "little while", however, is short in view of the millisecond scale of the plot. Date processing, curve fitting, and the predicting are done on a shorter time scale of microseconds than the plotted timescale of seconds.

Next, in the prediction time window that is indicated by vertical lines at 0 and about 1200, peaks at rising curves are located. These peaks here indicate instances where a stimulus should be given. This is further triggered of the frequency of the fitted curve and thus if the prediction is in a predefined frequency range. In other words, if the prediction has a frequency that is in a predetermined range, this provides a trigger for searching for certain events, here a peak after a rising EEG.

Figure 4:
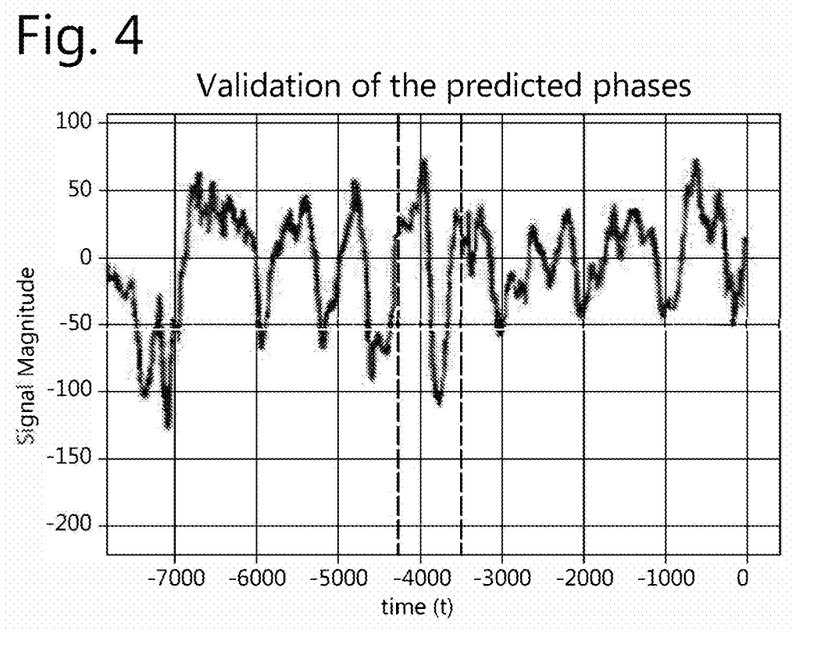
FIG. 4 shows the resulting stimulus validation based upon FIG. 5.

In FIG. 4, the timing of the stimulus is evaluated. In FIG. 4, a recorded EEG is plotted, showing the EEG of FIG. 3 about 4800 milliseconds later. Thus, what was the most recent time window in FIG. 4 is now at about t=−6800. Based upon the prediction in FIG. 3, two stimuli were given, one at about time t=600 and one at about time t=1300 on the scale of FIG. 3.

The actual EEG and the location of these stimuli is shown in FIG. 4, in order to check the actual EEG. The first stimulus at about time t=−4200 in FIG. 4 was at a peak after a steep rise, and the second stimulus at about time t=−3500 was also at a peak after a steep rise. Thus, FIGS. 3 and 4 show that the assembly allows the prediction of a future event in a brain signal, and providing a stimulus that can be timed using the prediction.

Figure 5:
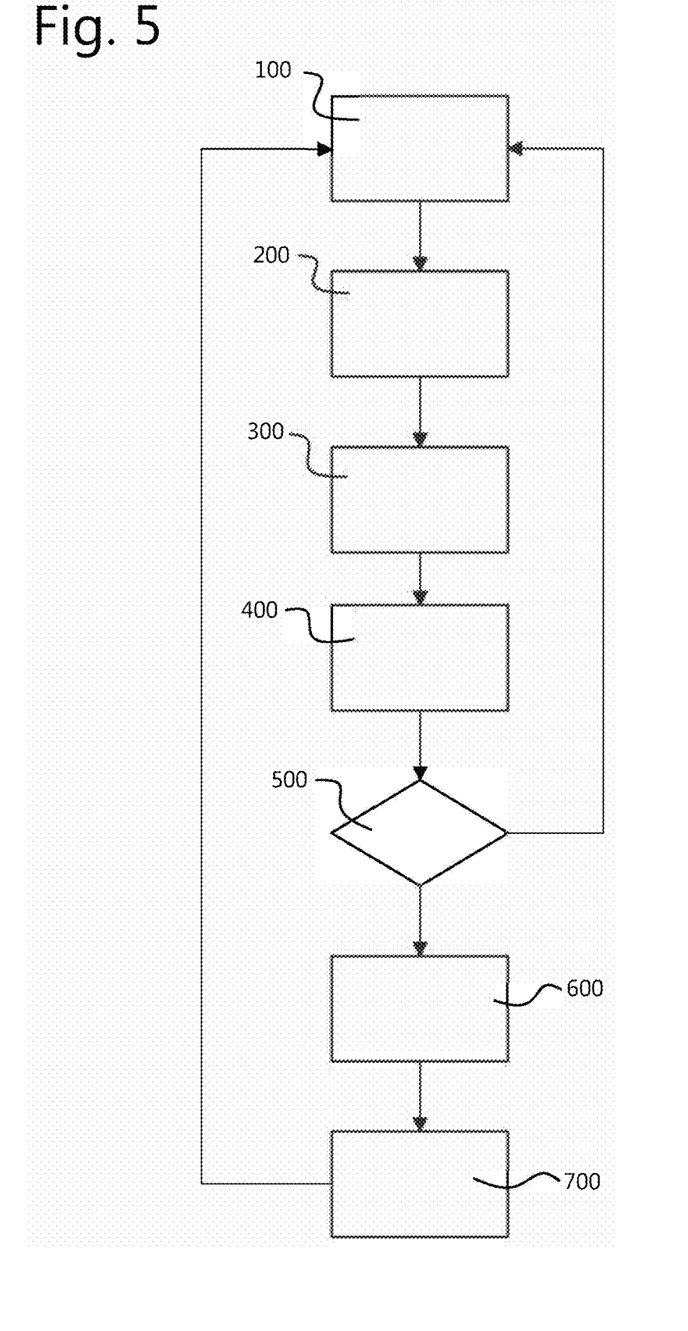
FIG. 5 shows a flow chart of possible program steps.

In FIG. 5, a schematic flowchart of a computer program is illustrated. The steps are explained on the basis of a example in which the brain-related signal is an EEG that is being recorded on a subject.
  100: retrieve an EEG data segment from a computer memory. The data segment is as close as possible to the current time.
  200: fit one or more curves to the retrieved EEG data segment.
  300: calculate a predicted EEG.
  400: detect one or more predefined features in the predicted EEG.
  500: if there is no event detected, go to step 100, if there is a predefined event detected, continue with step 600.
  600: calculate an event time. As explained, this event time will be in the future, allowing a stimulus to be applied to the subject in a time window around the predicted event time.
  700: actuate the stimulus generator for applying one or more stimuli to the subject.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

The invention claimed is:

1. A time-based brain-related signal influencing assembly comprising:
   a recording assembly for recording the time-based brain-related signal, the brain-related signal being a direct and unfiltered EEG signal;
   a stimulus generator for providing a stimulus, and
   a computer assembly functionally coupled to the recording assembly and to the stimulus generator, the computer assembly comprising:
   a memory for storing at least a data segment of the time-based brain-related signal during recording of the time-based brain-related signal and
   a computer program that, when running on the computer assembly, performs, in real-time, the steps of:
      retrieving a most-recent data segment of the stored data segment of the time-based brain-related signal;
      fitting at least one curve to the retrieved most-recent data segment;
      predicting a future continuation of the most-recent data segment using the at least one curve fitted to the most-recent data segment;
      detecting a predefined pattern in the predicted future continuation, and defining a predicted event time of the predefined pattern, the predicted event time being in the future with respect to the most-recent data segment, and
      after having defined the predicted event time, actuating the stimulus generator for providing the stimulus within a predefined event time window of the predicted event time;
   wherein fitting the at least one curve to the retrieved most-recent data segment comprises applying a non-linear regression algorithm;
   wherein the at least one curve comprises a series of periodic functions; and
   wherein the computer program performs the further steps of:
      calculating a reliability of the fit using the non-linear regression algorithm and,
      after having determined that the reliability is within a predefined criterion, releasing the stimulus within the predefined window of the predicted event time.

2. The assembly of claim 1, wherein the predicted future continuation extends at least 0.5 seconds beyond an end time of the most-recent data segment.

3. The assembly of claim 1, wherein the stimulus generator is arranged for applying a sensory discernible stimulus, and wherein the sensory discernible stimulus includes a sound or light stimulus that can be perceived by a human.

4. The assembly of claim 1, wherein the most-recent data segment has an end time that is less than 0.5 seconds from a current time of the assembly.

5. The assembly of claim 1, wherein the event time is in the future with respect to a current time of the brain-related signal-influencing assembly, whereby the brain-related signal-influencing assembly is allowed to apply the stimulus within the event time window.

6. The assembly of claim 1, wherein the at least one curve comprises a series of trigonometric functions, including sinusoidal functions.

7. The assembly of claim 1, wherein the computer program retrieves the most-recent data segment within a processing time less than 0.5 seconds from its recording.

8. The assembly of claim 1, wherein the most-recent data segment has a data window which has a width of less than 1 second.

9. The assembly of claim 1, wherein the computer program fits at least one periodic function to the most-recent data segment, the at least one periodic function having a period shorter than 2 seconds.

10. The assembly of claim 1, wherein the EEG has a time resolution of at least 100 samples per second.

11. The assembly of claim 1, wherein the predefined pattern is a predefined oscillatory phase in the brain-related signal, and the predefined pattern has a frequency in slow oscillation, alpha, or spindle range.

12. The assembly of claim 1, wherein criteria for stimulus release comprises a fitted sine that is in a predefined frequency range of interest reaching a combination of a fitting error threshold, reaching and a relative power threshold.

13. The assembly of claim 1, wherein the criteria for stimulus release is a fitted sine that is in a predefined frequency range of interest reaching a fitting error threshold.

14. The assembly of claim 1, wherein the criteria for stimulus release is a fitted sine that is in a predefined frequency range of interest reaching a relative power threshold.

15. A method for influencing a brain-related signal in a mammal the method comprising:
   retrieving a most-recent data segment of a stored data segment of the brain-related signal of the mammal, the brain-related signal being a direct and unfiltered EEG signal;
   fitting at least one curve to the retrieved most-recent data segment;
   predicting a future continuation of the most-recent data segment using the at least one curve fitted to the most-recent data segment;
   detecting a predefined pattern in the predicted future continuation, and defining a predicted event time of the predefined pattern, the predicted event time being in the future with respect to the most-recent data segment;
   actuating a stimulus generator for providing a stimulus within a predefined event time window of the predicted event time; and
   after having defined the predicted event time, providing the stimulus to the mammal,
   wherein fitting the at least one curve to the retrieved most-recent data segment comprises applying a non-linear regression algorithm;
   wherein the at least one curve comprises a series of periodic functions; and
   wherein the method further comprises:
   calculating a reliability of the fit using the non-linear regression algorithm and
   after having determined that the reliability is within a predefined criterion, releasing the stimulus within the predefined event time window of the predicted event time.

16. The method of claim 15, wherein the predicted future continuation extends at least 0.5 seconds beyond an end time of the most-recent data segment.

17. The method of claim 15, wherein the stimulus is a sensory discernible stimulus that that can be perceived by a human, wherein the sensory discernible stimulus is due to light.

18. The method of claim 15, wherein retrieving the most-recent data segment occurs less than half a second from an end time of the most-recent data segment.

19. The method of claim 15, wherein the at least one curve comprises a series of trigonometric functions, including sinusoidal functions.

20. The method of claim 15, wherein retrieving the most-recent data segment is performed within a processing time less than 0.5 seconds from its recording.

21. The method of claim 15, wherein the most-recent data segment has a data window with a width of less than 1 second.

22. The method of claim 15, wherein fitting at least one curve comprises fitting at least one periodic function to the most-recent data segment, the at least one periodic function having a period shorter than 2 seconds.

23. The method of claim 15, wherein the brain-related signal has a time resolution of at least 100 samples per second.

24. The method of claim 15, wherein the predefined pattern is a predefined oscillatory phase in the brain-related signal, and the predefined pattern has a frequency in the alpha or spindle range.

* * * * *